US008561611B2

(12) United States Patent
Shissler et al.

(10) Patent No.: US 8,561,611 B2
(45) Date of Patent: Oct. 22, 2013

(54) RESPIRATORY DEVICE MEASUREMENT SYSTEM

(75) Inventors: Andrew L. Shissler, Delmont, PA (US);
Patrick W. Truitt, Murrysville, PA (US);
William A. Truschel, Oakmont, PA (US)

(73) Assignee: RIC Investments, LLC, Wilmington, DE (US)

( * ) Notice: Subject to any disclaimer, the term of this patent is extended or adjusted under 35 U.S.C. 154(b) by 2251 days.

(21) Appl. No.: 11/449,194

(22) Filed: Jun. 8, 2006

(65) Prior Publication Data
US 2006/0283450 A1 Dec. 21, 2006

Related U.S. Application Data

(60) Provisional application No. 60/692,506, filed on Jun. 21, 2005.

(51) Int. Cl.
*A61M 16/00* (2006.01)
*A62B 7/00* (2006.01)
*F16K 31/02* (2006.01)

(52) U.S. Cl.
USPC ............. 128/204.21; 128/204.18; 128/204.22

(58) Field of Classification Search
USPC ............. 128/204.18, 204.21, 200.24, 204.26, 128/204.22, 204.23
See application file for complete search history.

(56) References Cited

U.S. PATENT DOCUMENTS

| 4,082,088 A * | 4/1978 | Franetzki et al. ............. 600/533 |
| 4,870,393 A * | 9/1989 | Snuttjer et al. ................ 340/611 |
| 5,303,700 A * | 4/1994 | Weismann et al. ...... 128/204.23 |
| 5,509,406 A * | 4/1996 | Kock et al. ............... 128/203.14 |
| 5,685,296 A | 11/1997 | Zdrojkowski et al. |
| 5,694,923 A | 12/1997 | Hete et al. |
| 5,937,855 A | 8/1999 | Zdrojkowski et al. |
| 6,017,315 A | 1/2000 | Starr et al. |
| 6,269,811 B1 | 8/2001 | Duff et al. |
| 6,371,113 B1 * | 4/2002 | Tobia et al. ............... 128/204.23 |
| 6,622,724 B1 | 9/2003 | Truitt et al. |
| 6,644,310 B1 | 11/2003 | Delache et al. |
| 2002/0077856 A1 | 6/2002 | Pawlikowski et al. |
| 2004/0159323 A1 | 8/2004 | Schmidt et al. |

OTHER PUBLICATIONS

PCT Search Report and Written Opinion, Dec. 18, 2006.

* cited by examiner

*Primary Examiner* — Justine Yu
*Assistant Examiner* — Colin W Stuart
(74) *Attorney, Agent, or Firm* — Michael W. Haas (57) ABSTRACT

A gas delivery system including a pressure generator, a pressure sensor, a control valve, and a processor. The pressure generator pressurizes breathable gas for delivery to a patient. The pressure sensor measures a pressure difference between the pressurized breathable gas and atmospheric pressure. The control valve is disposed downstream from the pressure generator and is constructed and arranged to control a flow rate of the pressurized breathable gas. The processor controls the control valve to bring the flow rate of the pressurized breathable gas to substantially zero while the pressure generator is operating and, when the flow rate is substantially zero, determines at least one of atmospheric pressure, an atmospheric air density, or a density correction factor based at least in part on the pressure difference between the pressurized breathable gas and the atmospheric pressure.

28 Claims, 4 Drawing Sheets

RESPIRATORY DEVICE MEASUREMENT SYSTEM

CROSS-REFERENCE TO RELATED APPLICATIONS

This application claims priority under 35 U.S.C. §119(e) from provisional U.S. Patent Application No. 60/692,506 filed Jun. 21, 2005 the contents of which are incorporated herein by reference.

BACKGROUND OF THE INVENTION

1. Field of the Invention

The invention relates to respiratory devices.

2. Description of the Related Art

Positive Airway Pressure (PAP) devices that deliver a pressurized flow of breathable gas to a patient are known. Typically, these PAP devices include a pressure generator that pressurizes the breathable gas, and one or more sensors for monitoring various parameters of the breathable gas and/or the ambient atmosphere. A PAP device usually uses the information received from the sensor(s) to control the pressure generator in a feedback loop to provide the breathable gas to the patient at a desired pressure and/or flow. The PAP device may also monitor the total amount of gas provided to the patient.

In order to provide an enhanced accuracy in determining the pressure, flow, and/or total volume of the breathable gas delivered to the patient, some PAP devices include various mechanisms, such as a barometric pressure sensor to monitor atmospheric pressure, to improve accuracy of measurement. While these sensors may enhance the accuracy of the determination of the pressure, flow and/or total volume of the breathable gas, they add to the total cost of the device.

SUMMARY OF THE INVENTION

The invention relates to a gas delivery system comprising a pressure generator, a pressure sensor, a control valve, and a processor. The pressure generator pressurizes breathable gas for delivery to a patient. The pressure sensor measures a pressure difference between the pressurized breathable gas and atmospheric pressure. The control valve is disposed downstream from the pressure generator and is constructed and arranged to control a flow rate of the pressurized breathable gas. The processor controls the control valve to bring the flow rate of the pressurized breathable gas to substantially zero while the pressure generator is operating and, when the flow rate is substantially zero, determines at least one of atmospheric pressure, an atmospheric air density, or a density correction factor based at least in part on the pressure difference between the pressurized breathable gas and the atmospheric pressure.

The invention also relates to a gas delivery system comprising a pressure generator, a pressure sensor, a flow sensor, and a processor. The pressure generator pressurizes breathable gas for delivery to a patient. The pressure sensor measures a pressure difference between the pressurized breathable gas and atmospheric pressure. The flow sensor measures a standard flow rate of the pressurized breathable gas output by the pressure generator. The processor determines at least one of atmospheric pressure, an atmospheric air density, or a density correction factor based at least in part on the pressure difference and the measured standard flow rate.

The invention further relates to a method of monitoring a pressurized breathable gas that is delivered to a patient. The method comprises pressurizing a breathable gas with a pressure generator, determining a pressure imparted to the breathable gas by the pressure generator, and determining at least one of atmospheric pressure, an atmospheric air density, or a density correction factor based at least in part on the pressure imparted to the breathable gas by the pressure generator.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
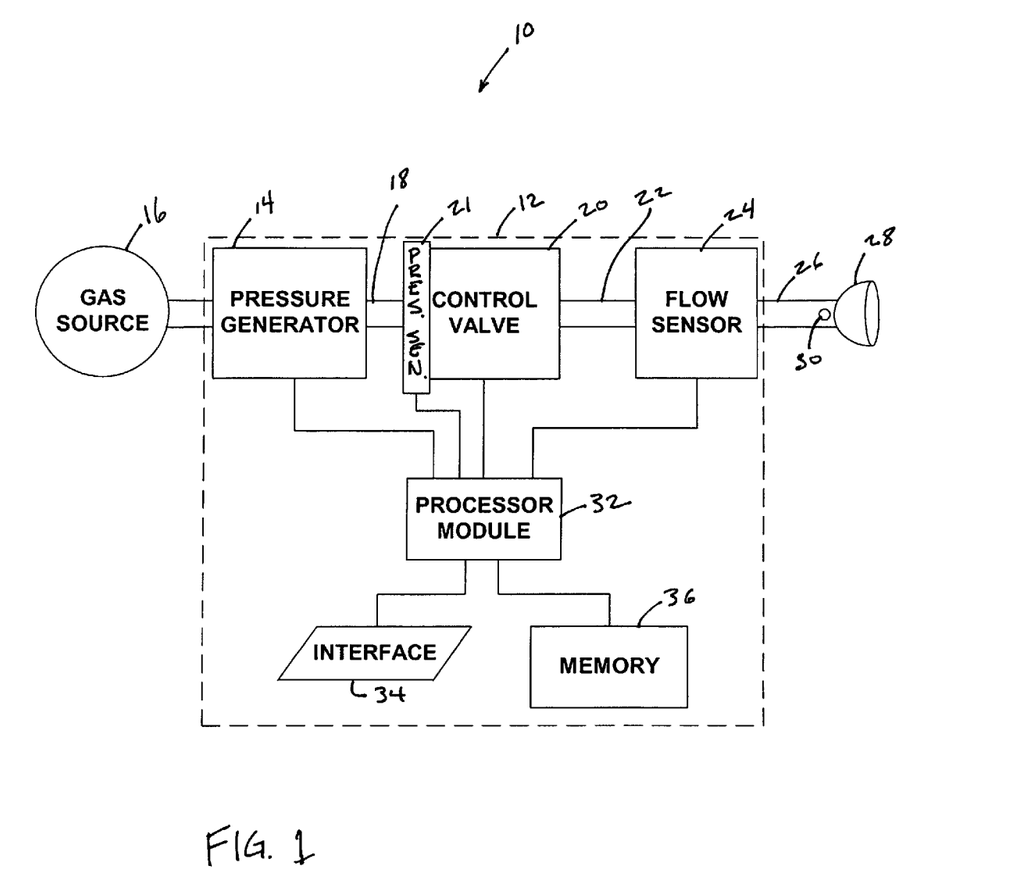
FIG. 1 is a schematic representation of a patient treatment system, according to an embodiment of the present invention.

FIG. 1 schematically illustrates an exemplary first embodiment of a patient treatment system 10 according to the principles of the present invention. Patient treatment system 10 generally includes a gas delivery system 12. The gas delivery system 12 controls a flow of breathable gas to a patient and includes a pressure generator 14 that receives a supply of breathable gas from a gas source 16. The gas source 16, in one embodiment, is simply atmospheric air. Pressure generator 14 elevates the pressure of gas from gas source 16 for delivery to the airway of the patient.

In one embodiment of the present invention, pressure generator 14 comprises a blower, as will be described later in greater detail in connection with FIG. 2. The blower can optionally be driven at a constant speed during the course of the pressure support treatment to produce a constant pressure or flow rate at its output 18. The present invention also contemplates that breathing gas source 16 can be any supply of breathing gas, such as air or an oxygen mixture, e.g., heliox, or a mixture of a breathing gas and a medication in gaseous form, such as nitric oxide.

In the illustrated embodiment, gas delivery system 12 includes a control valve 20. The elevated pressure flow of breathing gas from pressure generator 14 is delivered to the control valve 20 downstream of the pressure generator 14. Control valve 20, either alone or in combination with pressure generator 14, controls the final pressure or flow of gas 22 exiting the gas delivery system 12. Examples of a control valve 20 may include a sleeve or poppet valve, that exhausts gas from the patient circuit as a method of controlling the pressure in the patient circuit. As another example, U.S. Pat.

No. 5,694,923 to Hete et al., the contents of which are incorporated herein by reference, teaches a dual poppet valve system suitable for use as control valve 20 that exhausts gas to atmosphere and restricts the flow of gas from the pressure generator 14 to the patient.

In one embodiment, pressure generator 14 is a blower that operates at only one speed. In such an embodiment, control valve 20 alone controls the final pressure and flow rate for the breathing gas 22 delivered to the patient. However, the present invention also contemplates controlling the operating speed of the blower of pressure generator 14 in combination with control valve 20 to control the final pressure and flow rate for the breathing gas delivered to the patient. For example, a pressure or flow rate close to the desired pressure or flow rate can be set by establishing an appropriate operating speed for the blower (macro control). Fine tuning (micro control) of the pressure or flow rate can then be provided by control valve 20 so that the two, operating together, determine the final pressure for the breathing gas delivered to the patient.

The increase in pressure imparted to the breathable gas by pressure generator 14 can be measured by a pressure sensor 21 disposed between pressure generator 14 and control valve 20. More particularly, in one embodiment, pressure sensor 21 is disposed at or near an inlet of control valve 20 that receives the breathable gas from pressure generator 14. The pressure sensor 21 may take the form of a differential pressure sensor that measures the differential pressure of the breathable gas at or near the inlet of control valve 20. That is, pressure sensor 21 measures the difference between the pressure of the breathable gas at or near the inlet of control valve 20 and the atmospheric pressure. The differential pressure sensor is calibrated to measure the ambient pressure as zero pressure. Thus, the differential pressure sensor 21 measures a substantially zero pressure reading when pressure generator 14 is not operating, and measures changes in pressure in terms of the variation from this zero pressure (atmospheric pressure).

In the embodiment illustrated in FIG. 1, gas delivery system 12 also includes a flow sensor 24 for measuring a standard flow rate of the pressurized breathable gas. That is, flow sensor 24 is calibrated to assume that the pressurized breathable gas is at standard temperature (273 K) and standard pressure (1 atm), and thus provides what is termed the "standard flow rate." Because the flow sensor 24 measures "standard flow rate," that measurement may vary slightly from the volumetric flow rate because the temperature and pressure of the breathable gas will likely vary from standard temperature and pressure. Flow sensor 24 may include a device suitable for measuring standard flow rate, such as a hot-wire anemometer, spirometer, pneumotach, variable orifice transducer, or other conventional flow transducer. In the illustrated embodiment, flow sensor 24 is provided at a location relatively distant from a patient interface assembly. The present invention, however, contemplates locating flow sensor 24 at any location along a patient circuit 26 as well as at a patient interface assembly 28. For example, U.S. Pat. No. 6,017,315 to Starr et al., the contents of which are incorporated herein by reference, teaches a quantitative flow member that is located at the patient interface 28.

The flow of breathing gas is carried from gas delivery system 12 to the patient via patient circuit 26, which is typically a single flexible conduit that carries the flow of breathing gas to a patient interface assembly 28. Patient interface assembly 28 is any appliance, either invasive or non-invasive, such as a nasal mask, nasal/oral mask, total face mask, nasal cannula, endotracheal tube, or tracheal tube, suitable for communicating a supply of breathing gas to the airway of a patient. The patient interface assembly 28 may include headgear for mounting the appliance on the head of a patient. In the illustrated embodiment, the patient interface assembly 28 and/or patient circuit 26 includes a suitable exhaust port 30 for exhausting gas from these components to ambient atmosphere. Exhaust port 30 is preferably a passive exhaust port in the form of a continuously open port that imposes a flow restriction on the exhaust gas to permit control of the pressure of gas within patient interface assembly 28. It is to be understood, however, that exhaust port 30 can be an active exhaust port that assumes different configurations to control the exhaust rate. Examples of suitable exhaust ports are taught, for example, in U.S. Pat. Nos. 5,685,296 and 5,937,855 both to Zdrojkowski et al.

As shown in FIG. 1, gas delivery system 12 includes a processor module 32 that controls various operating aspects of gas delivery system 12. For example, the outputs of flow sensor 24 and pressure sensor 21 are provided to processor module 32 for processing, if needed, to determine the standard flow rate and the differential pressure of the breathable gas delivered to the patient.

A control interface 34 included in gas delivery system 12 provides data and commands to processor module 32. Although control interface 34 may include any device suitable to provide information and/or commands to processor module 32 via a hardwire or wireless connection, examples of control interface 34 may include a keypad, keyboard, touch pad, mouse, microphone, switches, button, dials, or any other devices that allow a user to input information to the patient treatment system 10.

The present invention also contemplates that the patient circuit 26 can be a two-limb circuit, which is common in conventional ventilators. The first limb, like patient circuit 26, delivers breathing gas to the patient, except that it lacks an exhaust port. Instead, the second limb carries the exhausted gases from the patient to ambient atmosphere. Typically, an active exhaust port in the second limb under the control of a controller (e.g. processor module 32) provides the desired level of positive end expiratory pressure (PEEP) to the patient. In addition, gas delivery system 12 and related components can include other conventional devices and components, such as a humidifier, heater, bacteria filter, humidity sensor, and a gas sensor (e.g., a capnometer), that filter, measure, monitor, and analyze the flow of gas to or from the patient.

Processor module 32 controls the actuation of control valve 20, thereby controlling the pressure of the breathing gas delivered to the patient. Processor module 32 is suitably programmed with an algorithm or algorithms for calculating the pressure to be applied to the patient according to various modes of ventilation. In a more advanced embodiment of the present invention, the processor module 32 optionally includes a memory 36 associated with gas delivery system 12 that stores the programming necessary to perform any of a plurality of modes of ventilation, depending on which mode of ventilation is selected by the caregiver or patient using control interface 34. Memory 36 is also capable of storing data regarding the operation of the patient treatment system 10, input commands, alarm thresholds, as well as any other information pertinent to the operation of the patient treatment system, such as measured values of patient flow, volume, pressure, device usage, operating temperatures, and motor speed.

Figure 2:
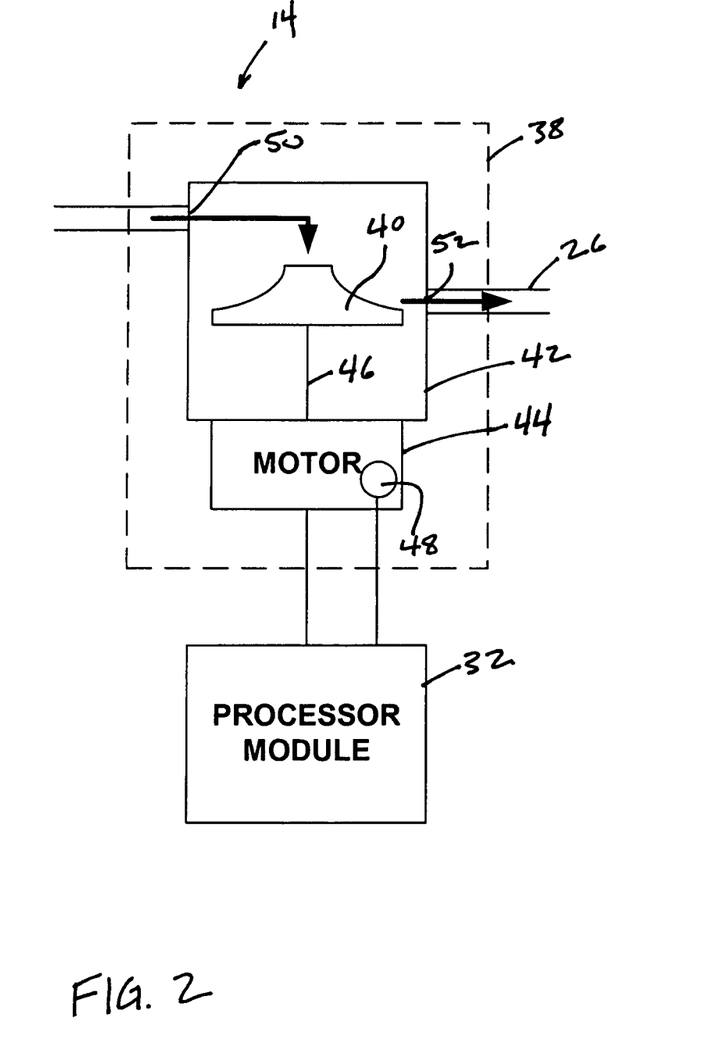
FIG. 2 is an exemplary illustration of a pressure generator, in accordance with an embodiment of the present invention.

FIG. 2 is an exemplary illustration of a pressure generator 14 according to an embodiment of the invention. The pressure generator 14 comprises a blower 38 that receives the breathable gas from gas source 16 (not shown in FIG. 2), and elevates the pressure of the breathable gas for delivery to the patient at a pressure that is greater than the ambient, i.e., atmospheric, pressure. The pressurized flow of breathable gas is then carried to the patient by patient circuit 26.

As is shown in FIG. 2, blower 38 includes an impeller 40 disposed within a housing 42. A motor 44 coupled to a drive shaft 46 rotates impeller 40. The breathable gas is delivered to the center of impeller 40 via a blower inlet 50. Rotation of impeller 40 applies a force to the breathable gas, thereby pressurizing the gas and propelling the gas out of blower 38 at a blower outlet 52. The operation of motor 44 is controlled by processor module 32. In one embodiment of the present invention, processor module 32 is capable of adjusting the speed of motor 44 to set the desired pressure to be output by pressure generator 14. To this end, conventional controls, which may be included in control interface 34, are provided for providing inputs to processor module 32, for example to select the desired output pressure, and, hence, the operating speed of motor 44. The operating speed of motor 44 is measured by a tachometer 48 that is in operative communication with processor module 32. U.S. Pat. No. 6,622,724 to Truitt et al., the contents of which are incorporated herein by reference, describes with greater particularity a blower and impeller that may be implemented as blower 38 and impeller 40, in one embodiment of the invention.

In other embodiments of the present invention, the pressure generator 14 can be a piston, a pump, or a bellows without departure from the principles set forth herein.

Referring back to FIG. 1, during the operation of gas delivery system 12, processor module 32 determines various parameters of the flow of breathable gas delivered to the patient that are not directly measured by pressure sensor 21 and flow sensor 24. For example, processor 32 may determine an atmospheric pressure (i.e., barometric pressure), an atmospheric air density, a volumetric flow rate of the pressurized breathable gas, or other parameters. The determination of these parameters, among other things, enables processor module 32 to monitor the volume of the breathable gas delivered to patient interface assembly 28.

The volume of breathable gas delivered to patient interface assembly 28 is dependent on the volumetric flow rate of the pressurized breathable gas. However, the flow measured by flow sensor 24 is the standard flow rate, which would be equivalent to the volumetric flow rate (actual volume flow of gas) if the pressure and temperature of the breathable gas were at standard conditions (e.g., 273 K and 1 atm). The relationship between the volumetric flow rate and the standard flow rate can be expressed as follows:

$$(1) Q_{vol} = Q_{std} * C;$$

where $Q_{vol}$ represents the volumetric flow rate, $Q_{std}$ represents the standard flow rate, and C represents a density correction factor. Thus, it is possible to determine or approximate the volumetric flow rate based upon the standard flow rate measured by flow sensor 24, and by determining the density correction factor. For the purposes of this disclosure, the "density correction factor" is the proportionality factor that is multiplied by the standard flow rate of a flow of gas to determine the volumetric flow rate of the gas. The density correction factor is a function of the ambient conditions surrounding and within gas delivery system 12 such as ambient pressure, ambient temperature, and/or ambient air density. For example, the density correction factor may be determined according to the following:

$$2. \ C = \left(\frac{T_m}{T_{std}}\right)\left(\frac{P_{std}}{P_m}\right);$$

which can be re-written, using the ideal gas law, as:

$$3. \ C = \frac{\rho_{std}}{\rho_m};$$

where $T_m$ represents a measured absolute temperature, $T_{std}$ represents standard temperature, $P_{std}$ represents standard pressure, $P_m$ represents a measured absolute pressure, $\rho_{std}$ represents standard air density, and $\rho_m$ represents a measured air density.

In order to determine the density correction factor according to one of the relationships expressed in equations (2) or (3), the processor module 32 first calculates either a measured absolute pressure (Eqn. 2) or a measured air density (Eqn. 3). By making several assumptions, including the assumption that the pressurization of the breathable gas is an isothermal process and the assumption that the pressure applied to any differential volume of gas along impeller 44 is a function of only the distance between the differential volume and the axis of rotation of impeller 44 (i.e., drive shaft 46), the increase in pressure applied by blower 38 to the breathable gas can be expressed as follows:

$$4. \ \Delta P = P_{inlet} * \left(e^{\frac{\omega^2 \cdot r^2}{2 \cdot R \cdot T}} - 1\right);$$

where $\Delta P$ represents the increase in pressure applied by blower 38, $P_{inlet}$ represents a pressure of the breathable gas at blower inlet 50, $\omega$ represents the angular frequency of impeller 40, r represents the radius of impeller 40, R represents the gas constant for the breathable gas, and T represents the temperature of the breathable gas.

In order to determine the atmospheric pressure by implementing equation (4), control valve 20 is closed while blower 38 is running, effectively lowering the flow of the breathable gas (both standard and volumetric) to zero (or substantially zero), which causes the pressure of the breathable gas at blower inlet 50 ($P_{inlet}$) to be equal (or substantially equal) to the atmospheric pressure. This is because the gas source 16 being used is simply atmospheric air. Since pressure sensor 21 is disposed upstream from (or prior to) control valve 20, and measures the difference between the atmospheric pressure (now equal to the pressure at blower inlet 50) and absolute pressure of the breathable gas that has been pressurized by blower 38 but is blocked by the closed control valve 20, the differential pressure measured by pressure sensor 21 is substantially equal to the pressure applied to the breathable gas by the blower 38 ($\Delta P$). Based on these relationships, equation (4) may be solved for atmospheric pressure to yield the following:

$$5. \ P_{atm} = \frac{P_{diff}}{e^{\frac{\omega^2 \cdot r^2}{2 \cdot R \cdot T}} - 1};$$

where $P_{atm}$ represents the atmospheric pressure, and $P_{diff}$ represents the differential pressure measured by pressure sensor 21. In one embodiment, the temperature of the breathable gas may be measured directly, such as by a thermometer or other temperature sensor, although this would add cost to the device. Thus, in another embodiment, the temperature may be estimated based on typical operating conditions. In one embodiment, the temperature of the breathable gas is assumed to be approximately 315 degrees Kelvin. In such an embodiment, flow sensor 24 may include a sensor that compensates somewhat for temperature in measuring the standard flow rate of the pressurized gas. For example, flow sensor 24 may include a hot-wire anemometer that includes a core comprising an exposed hot wire either heated up by a constant current or maintained at a constant temperature. In such an embodiment, the fluid velocity of the pressurized breathable gas may be measured as a function of the heat convected away by the pressurized breathable gas. As should be appreciated, since such an anemometer would rely on a detection of the temperature of the gas (which would be influenced by the ambient temperature at the sensor, as well as the convection of the pressurized breathable gas), the determination standard flow made from this detection would partially compensate for the ambient temperature at the sensor.

Since the atmospheric pressure typically remains relatively stable for time periods over which patient treatment system 10 would typically be used by the patient (e.g., overnight), in one embodiment the atmospheric pressure is measured only once, during start-up, and assumed to remain constant, that is, control valve 20 is closed, after blower 38 has been brought up to an operating speed, at the start-up of gas delivery system 12 for a treatment session, to enable processor module 32 to make a single determination of atmospheric pressure at the beginning of the treatment session. The atmospheric pressure is assumed to be constant throughout the session. In another embodiment, control valve 20 may be closed to enable re-calculation of the ambient pressure at pauses during the treatment session.

In other embodiments, the atmospheric pressure may be determined without closing control valve 20. For example, in single limb systems, like patient treatment system 10, the patient exhales into patient circuit 26 against the flow of the breathable gas delivered by gas delivery system 10. These exhalations may, at least instantaneously, bring the flow of pressurized gas to substantially zero, as the gas leaving the airway of the patient is forced back up patient circuit 26 toward gas delivery system 12 against the pressurized flow of breathable gas. The absence of flow throughout gas delivery system 12, due to patient exhalation, or other phenomena, creates substantially the same conditions as the closing of control valve 20. This enables processor module 32 to implement equation (5) to determine the current atmospheric pressure from the measurements of pressure sensor 21, tachometer 48, and a temperature sensor (or with an assumed temperature if patient treatment system 10 does not include a temperature sensor). In this embodiment, a detection by flow sensor 24 of an instantaneous flow of zero (or substantially zero) may act as a predetermined trigger event that triggers processor module 32 to re-calculate the current atmospheric pressure.

Once the atmospheric pressure is determined, the absolute pressure of the breathable gas may be detected by adding the differential pressure detected by pressure sensor 21 to the atmospheric pressure previously determined (e.g., $P_m = P_{atm} + P_{diff}$). Using the measurement of the absolute pressure, the density correction factor is then monitored by processor module 32 by inserting the absolute pressure of the breathable gas into equation (2), along with the temperature of the breathable gas. From the calculation of the density correction factor, and the measurement of the standard flow rate by flow sensor 24, processor module 32 monitors the volumetric flow rate of the breathable gas according to equation (1). Monitoring the volumetric flow rate of the breathable gas enables the processing module to determine the total volume of breathable gas delivered by gas delivery system 12, and adjust the operation of pressure generator 14 and/or control valve 20 based on the specific parameters of the breathable gas and the ambient conditions. For example, processing module 32 may reduce the speed of motor 44 based on a determination of an elevated atmospheric pressure (or an elevated air density). Reducing the speed of motor 44 reduces the noise created by gas delivery system 12 and reduces the power used by gas delivery system 12, and reduces wear and tear on various components of blower 38 (e.g., impeller 40, motor 44, and drive shaft 46), among other things.

In one embodiment, the processor module 32 monitors the density of the pressurized breathable gas according to the ideal gas law as follows:

$$6.\ \rho_m = \frac{P_m}{R \cdot T}. \tag{6}$$

In this embodiment, the processor module 32 may monitor the density correction factor by inserting this calculation for the density of the pressurized gas into equation (3), rather than employing equation (2) as was described above.

Figure 3:
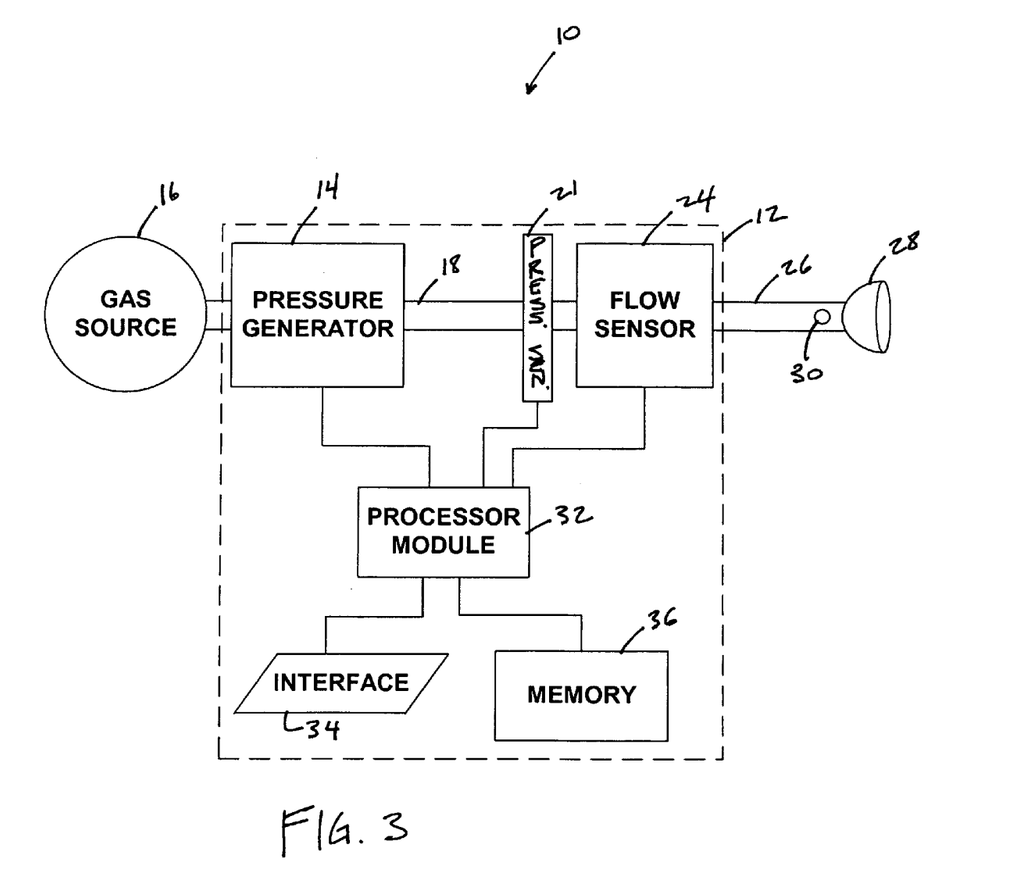
FIG. 3 illustrates an alternative configuration of the patient treatment system according to an embodiment of the present invention.

It will be appreciated that the configuration of patient treatment system 10 illustrated in FIG. 1 is not intended to be limiting, and that the scope of the invention includes any other configuration that enables processor module 32 to monitor the volumetric flow rate and/or air density of the pressurized gas to the patient, and/or the atmospheric pressure without directly measuring these parameters. For example, FIG. 3 illustrates a configuration of patient treatment system 10 according to an embodiment of the present invention in which gas delivery system 12 does not include control valve 20. In FIG. 3, like parts are given the same reference numerals as in FIGS. 1 and 2.

In the configuration of patient treatment system 10 illustrated in FIG. 3, gas delivery system 12 controls the pressure of the breathable gas delivered to the patient based only on the output of pressure generator 14. That is, processor module 32 controls the pressure of breathing gas delivered to the patient by controlling only the motor speed of pressure generator 14, which may again take the form of blower 38. According to this embodiment, processor module 32 may control pressure generator 14 in a feedback manner based on one or more of the measuring of the pressure of the breathable gas by pressure sensor 21 and/or tachometer 48 (see FIG. 2).

Since the configuration of gas delivery system 12 shown in FIG. 3 does not include control valve 20, the flow of the pressurized breathable gas cannot be controllably brought to zero by processor module 32 while pressure generator 14 is running. However, processor module 32 may still determine the atmospheric pressure according to equation (5) when the instantaneous flow of the pressurized breathable gas reaches zero, for example, when the flow rate instantaneously reaches zero due to patient exhalation, or through some other mechanism or phenomena that brings the flow of the breathable gas to zero. Based on the determination (or determinations) of atmospheric pressure, the processing module may monitor the density of the pressurized breathable gas, the volumetric flow rate of the breathable gas, or other parameters of the breathable gas, as was described above.

According to one aspect of the invention, the measured atmospheric pressure, the atmospheric air density, and/or the density correction factor can be used by the processor 32 in a feedback loop to control various aspects of the patient treatment system 10. For example, the processor 32 can be used to control operation (e.g., speed and output) of the pressure generator 14. In addition, in embodiments in which the control valve 20 is provided, the processor 32 can be used to control the operation of valve 20 to regulate flow to the patient. Control of the pressure generator 14 and/or valve 20 with the processor 32 being provided, the added information in accordance with the above disclosure can enable an enhanced control and measurement of output flow to a patient.

Figure 4:
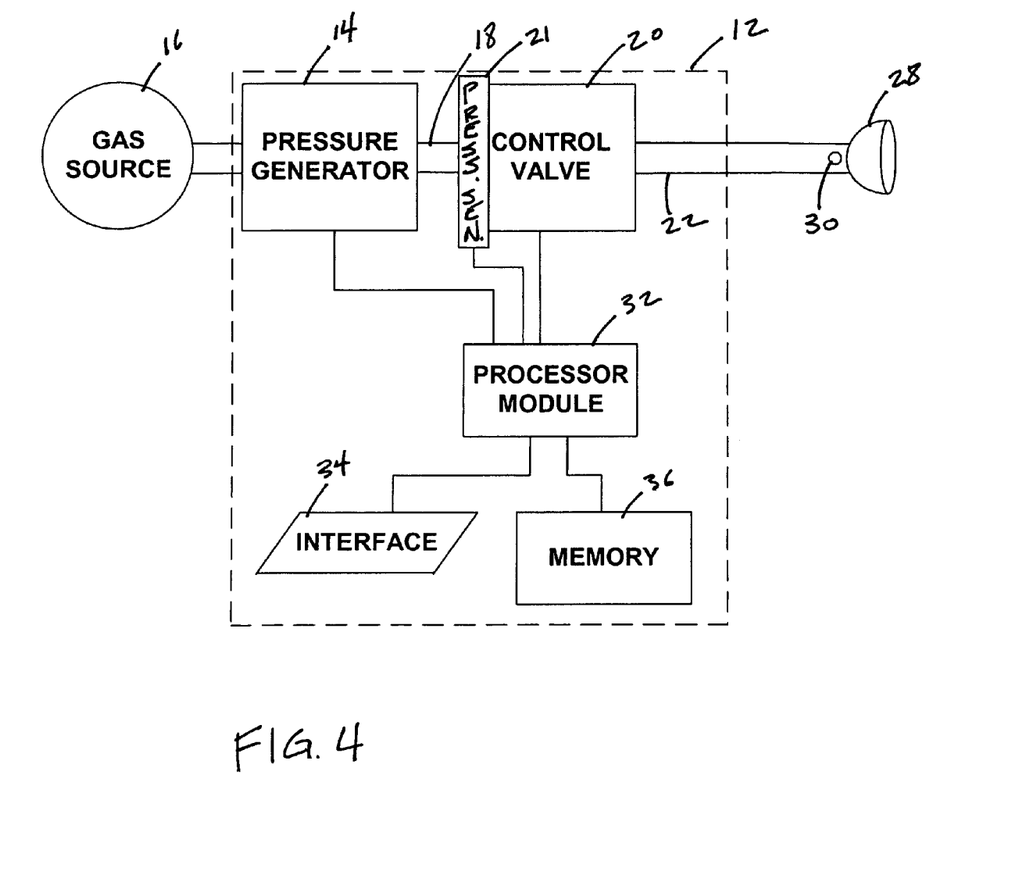
FIG. 4 is an exemplary illustration of an alternative configuration of the patient treatment system, in accordance with an embodiment of the present invention.

FIG. 4 illustrates an alternate configuration of patient treatment system 10 according to yet another embodiment of the invention. Again, like parts are given like reference numerals. More particularly, in the configuration of patient treatment system 10 shown in FIG. 4, gas delivery system 12 does not include flow sensor 24. However, processor module 32 may still determine the atmospheric pressure according to equation (5) by closing control valve 20, measuring differential pressure ($P_{diff}$) with pressure sensor 21, and assuming (rather than measuring) a flow of zero. Based on this determination, processor module 32 may monitor the various parameters of the pressurized breathable gas described above while the gas delivery system 12 operates.

It will be appreciated that the specific equations presented above have been provided merely for illustrative purposes only, and that the intended scope of the invention encompasses alternate algorithms for monitoring parameters of the breathable gas that are a function of the atmospheric pressure without directly measuring the atmospheric pressure.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A gas delivery system comprising:
    a pressure generator that pressurizes breathable gas for delivery to a patient;
    a pressure sensor that measures a pressure difference between the pressurized breathable gas and atmospheric pressure;
    a flow sensor that measures a standard flow rate of the pressurized breathable gas output by the pressure generator; and
    a processor that determines at least one of atmospheric pressure, an atmospheric air density, or a density correction factor based at least in part on the pressure difference and the measured standard flow rate.

2. The system of claim 1, wherein the flow sensor is a hot wire anemometer.

3. The system of claim 2, wherein the processor is triggered to determine at least one of the atmospheric pressure, the atmospheric air density, and the density correction factor upon a detection of a predetermined triggering event.

4. The system of claim 3, wherein the predetermined triggering event comprises the pressurized breathable gas having a standard flow rate of substantially zero.

5. The system of claim 1, further comprising a valve downstream from the pressure generator, the valve being controlled by the processor.

6. The system of claim 1, wherein the processor determines the density correction factor and multiplies the standard flow rate of the pressurized breathable gas by the density correction factor to determine a volumetric flow rate of the pressurized breathable gas.

7. The system of claim 1, further comprising a temperature monitor that monitors the temperature of the pressurized breathable gas.

8. The system of claim 7, wherein the processor determines the at least one of the atmospheric pressure, the atmospheric air density, or the density correction factor also based at least in part on the temperature of the pressurized breathable gas.

9. The system of claim 1, wherein the pressure generator comprises a blower, the blower further comprising:
    a motor associated with the blower; and
    an impeller associated with the blower, the impeller being rotatably driven by the motor to pressurize the breathable gas, wherein the processor determines the at least one of the atmospheric pressure, the atmospheric air density, and the density correction factor also based at least in part on a dimension of the impeller and a rotational velocity at which the impeller is driven.

10. The system of claim 9, further comprising a tachometer that monitors the rotational velocity at which the impeller is driven.

11. The system of claim 1, wherein the processor assumes that the pressurization of the breathable gas is an incompressible, isothermal process.

12. A gas delivery system comprising:
    a pressure generator that pressurizes breathable gas for delivery to a patient;
    a pressure sensor that measures a pressure difference between the pressurized breathable gas and atmospheric pressure;
    a control valve disposed downstream from the pressure generator, the control valve constructed and arranged to control a flow rate of the pressurized breathable gas; and
    a processor that controls the control valve to bring the flow rate of the pressurized breathable gas to substantially zero while the pressure generator is operating and, when the flow rate is substantially zero, determines at least one of atmospheric pressure, an atmospheric air density, or a density correction factor based at least in part on the pressure difference between the pressurized breathable gas and the atmospheric pressure.

13. The system of claim 12, further comprising a flow sensor disposed downstream from the pressure generator, the flow sensor measuring a standard flow rate of the pressurized breathable gas.

14. The system of claim 13, wherein the processor determines the density correction factor and multiplies the standard flow rate of the pressurized breathable gas by the density correction factor to determine a volumetric flow rate of the pressurized breathable gas.

15. The system of claim 12, wherein the processor assumes that the pressurization of the breathable gas is an incompressible, isothermal process.

16. The system of claim 12, wherein the processor controls operation of the pressure generator based on at least one of the atmospheric pressure, the atmospheric air density, or the density correction factor.

17. A method of monitoring a pressurized breathable gas that is delivered to a patient, the method comprising:
    (a) pressurizing a breathable gas with a pressure generator;
    (b) determining a pressure imparted to the breathable gas by the pressure generator; and
    (c) determining at least one of atmospheric pressure, an atmospheric air density, or a density correction factor based at least in part on the pressure imparted to the breathable gas by the pressure generator.

18. The method of claim 17, further comprising: determining a standard flow rate of the pressurized breathable gas, and wherein the determining step (c) is also based at least in part on the standard flow rate.

19. The method of claim 18, wherein the standard flow rate of the pressurized breathable gas is determined by measuring the standard flow rate with a flow sensor.

20. The method of claim 19, wherein the flow sensor is a hot wire anemometer.

21. The method of claim 19, further comprising detecting a predetermined triggering event, and wherein the step of determining at least one of an atmospheric pressure, an air density, or a density correction factor is triggered by the detection of the predetermined triggering event.

22. The method of claim 21, wherein the predetermined triggering event comprises determining that the pressurized breathable gas has a standard flow of substantially zero.

23. The method of claim 17, further comprising: bringing the flow rate of the pressurized breathable gas to substantially zero, and wherein the determining step (c) is also based at least in part on an assumption that the standard flow rate is zero.

24. The method of claim 23, wherein bringing the standard flow rate of the pressurized breathable gas to substantially zero comprises closing a valve.

25. The method of claim 17, further comprising determining a temperature of the pressurized breathable gas.

26. The method of claim 25, wherein the determination of at least one of the atmospheric pressure, the atmospheric air density, or the density correction factor is based at least in part on the pressure imparted to the breathable gas by the pressure generator, and the temperature of the pressurized breathable gas.

27. The method of claim 17, further comprising: controlling the pressure generator based at least in part on at least one of the atmospheric pressure, the atmospheric air density, or the density correction factor.

28. The method of claim 17, wherein the pressure generator includes a control valve for controller a pressure of the breathable gas, the method further comprising: controlling the control valve based at least in part on at least one of the atmospheric pressure, the atmospheric air density, or the density correction factor.

* * * * *